（12）United States Patent
Kanamaru et al.

(10) Patent No.: US 9,273,332 B2
(45) Date of Patent: Mar. 1, 2016

(54) METHOD FOR PRODUCTION OF L-AMINO ACID

(75) Inventors: Hiroyuki Kanamaru, Takasago (JP); Makoto Ueda, Takasago (JP); Hirokazu Nanba, Takasago (JP)

(73) Assignee: Kaneka Corporation, Osaka (JP)

( * ) Notice: Subject to any disclaimer, the term of this patent is extended or adjusted under 35 U.S.C. 154(b) by 873 days.

(21) Appl. No.: 12/445,233

(22) PCT Filed: Oct. 11, 2007

(86) PCT No.: PCT/JP2007/069805
§ 371 (c)(1),
(2), (4) Date: Jun. 8, 2009

(87) PCT Pub. No.: WO2008/047656
PCT Pub. Date: Apr. 24, 2008

(65) Prior Publication Data
US 2010/0028959 A1    Feb. 4, 2010

(30) Foreign Application Priority Data

Oct. 12, 2006    (JP) ................................ 2006-279075

(51) Int. Cl.
| | |
|---|---|
| C12P 13/06 | (2006.01) |
| C12P 13/08 | (2006.01) |
| C12P 13/22 | (2006.01) |
| C12P 13/04 | (2006.01) |
| C12N 9/02 | (2006.01) |

(52) U.S. Cl.
CPC ................. *C12P 13/06* (2013.01); *C12P 13/04* (2013.01); *C12P 13/08* (2013.01); *C12P 13/222* (2013.01); *C12N 9/0008* (2013.01); *C12N 9/0073* (2013.01)

(58) Field of Classification Search
CPC .......... C12P 13/04; C12P 13/06; C12P 13/08; C12P 13/22; C12P 13/222; C12N 9/0073; C12N 9/0008
See application file for complete search history.

(56) References Cited

U.S. PATENT DOCUMENTS

| 4,849,345 A | | 7/1989 | Asano et al. | |
|---|---|---|---|---|
| 5,034,320 A | * | 7/1991 | Endo .............................. | 435/119 |
| 5,225,593 A | * | 7/1993 | Imanari et al. ................ | 562/538 |
| 2004/0115691 A1 | | 6/2004 | Rozzell et al. | |
| 2006/0063238 A1 | | 3/2006 | Hummel et al. | |
| 2008/0145904 A1 | * | 6/2008 | Groger et al. .................. | 435/157 |
| 2008/0153140 A1 | * | 6/2008 | Gupta et al. ................... | 435/132 |

FOREIGN PATENT DOCUMENTS

| EP | 0692538 A2 | 1/1996 |
|---|---|---|
| EP | 1995314 A1 | 11/2008 |
| JP | 62-244386 A | 10/1987 |
| JP | 63-258590 A | 10/1988 |
| JP | 10-23896 A | 1/1989 |
| JP | 06-086639 A | 3/1994 |
| JP | 2002-171993 A | 6/2002 |
| JP | 2002171993 A | 6/2002 |
| JP | 2003-284583 A | 10/2003 |
| JP | 2004-159587 A | 6/2004 |
| WO | WO-2005/093081 A1 | 10/2005 |
| WO | WO 2005093081 A1 * | 10/2005 |
| WO | WO-2006/015885 A1 | 2/2006 |
| WO | WO 2006087235 A1 * | 8/2006 |
| WO | WO-2007/114217 A1 | 10/2007 |

OTHER PUBLICATIONS

English translation of JP 6224386, inventor Asano, by FLS, Inc. Oct. 2011.*
Kotz et al. "Chemistry and Chemical Reactivity" second edition (1991) (Saunder College Publishing: Ft. Worth) pp. 609-611.*
Sigma Catalog (1995) (Sigma Chemcial Co.: St. Louis MO) p. 896.*
definition of purity by ehow.com website http://.ehow.com/facts_5530150_defintion-purity.html downloaded Nov. 17, 2014.*
definition of upon from dictionary.com website http://dictionary.reference.com/browse/upn dowloaded Nov. 17, 2014.*
defintion of "addition" downloaded from http://www.thefreedictionary.com/addition on May 9, 2015.*
defintion of "chemical purity" http://medical-dictiionary.com/chemical+purity downloaded May 10, 2015.*
English translation of International Preliminary Report on Patentability for International Application No. PCT/JP2007/069805.
Patel et al., "Enzymatic synthesis of chiral intermediates for Omapatrilat, an antihypertensive drug", Biomol Eng, vol. 17 (6), pp. 167-182, Jun. 2001.
Lin et al., Continuous Production of L-Alanine with NADH Regeneration by Nanofiltration Membrane Reactor, Biosci. Biotech. Biochem., 61 (12), 2029-2033, 1997.
Lin et al., "Nanofiltration Membrane Bioreactor for Continuous Asymmetric Reduction of 2-Ketoglutarate to Produce L-Glutamate with NADH Regeneration." Journal of Fermentation and Bioengineering, 83, (1), 54-58, 1997.
Jeffries et al., "Bioconversion of Secondary Fiber Fines to Ethanol Using Counter-Current Enzymatic Saccharificaton and Co-Fermentation", Applied Biochemistry and Biotechnology, vol. 77-79, pp. 435-444 (1999).

* cited by examiner

*Primary Examiner* — Susan Hanley
(74) *Attorney, Agent, or Firm* — Novak Druce Connolly Bove + Quigg LLP

(57) ABSTRACT

The present invention has its object to provide a method for producing an L-amino acid comprising reacting a keto acid with an amino acid dehydrogenase and an enzyme having coenzyme regenerating ability to convert to a L-amino acid, wherein a coenzyme is added in two or more portions in the reaction. The method of the present invention enables efficient production of an L-amino acid useful as a synthetic intermediate such as a pharmaceutical intermediate with high optical purity by an enzymatic reductive amination independent of the purity of the keto acid used as a substrate.

20 Claims, No Drawings

SEQUENCE LISTING

```
<160> NUMBER OF SEQ ID NOS: 4

<210> SEQ ID NO 1
<211> LENGTH: 27
<212> TYPE: DNA
<213> ORGANISM: Artificial
<220> FEATURE:
<223> OTHER INFORMATION: Primer-1

<400> SEQUENCE: 1
atcacgcata tggcgaaaat actttgc                                          27

<210> SEQ ID NO 2
<211> LENGTH: 30
<212> TYPE: DNA
<213> ORGANISM: Artificial
<220> FEATURE:
<223> OTHER INFORMATION: Primer-2

<400> SEQUENCE: 2
atagaattct tatcagccgg ccttcttgaa                                       30

<210> SEQ ID NO 3
<211> LENGTH: 43
<212> TYPE: DNA
<213> ORGANISM: Artificial
<220> FEATURE:
<223> OTHER INFORMATION: Primer-3

<400> SEQUENCE: 3
actgaattct aaggaggtta acaatggaac tttttaaata tat                        43

<210> SEQ ID NO 4
<211> LENGTH: 32
<212> TYPE: DNA
<213> ORGANISM: Artificial
<220> FEATURE:
<223> OTHER INFORMATION: Primer-4

<400> SEQUENCE: 4
gatgagctct tattaacgtc tgcttaatac ac                                    32
```

METHOD FOR PRODUCTION OF L-AMINO ACID

CROSS REFERENCE TO RELATED APPLICATIONS

This application is a National Stage of PCT/JP2007/069805 filed Oct. 11, 2007 which in turn claims priority from Japanese Application 2006-279075 filed Oct. 12, 2006, the entire contents of which are incorporated herein by reference.

TECHNICAL FIELD

The present invention relates to a method for producing an L-amino acid useful as an intermediate such as a pharmaceutical intermediate. More specifically, the present invention relates to a method for producing an L-amino acid comprising reacting a keto acid corresponding to a target amino acid with an amino acid dehydrogenase and an enzyme having coenzyme regenerating ability to convert to the target L-amino acid, wherein a coenzyme is added in two or more portions in the reaction.

BACKGROUND ART

L-amino acids are useful as synthetic intermediates such as pharmaceutical intermediates. Various methods for producing an L-amino acid are known such as an extraction method, a chemical synthesis method, a fermentation method, and an enzymatic synthesis method. The extraction method requires large-scale purification equipment for purification of a target amino acid from protein hydrolysates. Because amino acids produced in the chemical synthesis method are typically racemates, the chemical synthesis method requires an expensive resolving agent, asymmetric catalyst or the like for production of the optically active isomers. The fermentation method produces products at low concentrations, and requires large-scale purification equipment like the extraction method. In addition, the fermentation method is not suitable for synthesis of normatural amino acids. The enzymatic synthesis method can be used to provide a lower-cost, efficient production method that overcomes these problems by using an inexpensive biocatalyst. For example, a method for producing an L-amino acid in which a keto acid corresponding to a target amino acid is reacted with an amino acid dehydrogenase and an enzyme having coenzyme regenerating ability to produce the target L-amino acid (Non-Patent Document 1) is known as an enzymatic synthesis method for producing an L-amino acid. However, the above-mentioned method requires an expensive commercial enzyme or an enzyme purified from a microorganism, and its industrial use has been problematic.

In order to solve such problems, high production methods of these enzymes have been under development in which DNAs encoding these enzymes are cloned using gene recombinant techniques to obtain a transformant, and the transformant is cultured. For example, a method has been known in which a transformant containing a gene encoding a coenzyme-dependent amino acid dehydrogenase and a gene encoding a coenzyme regenerating enzyme is prepared and cultured, and then allowed to act on a keto acid to produce an L-amino acid (Patent Documents 1 and 2). However, the reaction described in Patent Document 1 produces an L-amino acid at a concentration of about 10 mM, which is low for industrial production. In the method described in Patent Document 2, a keto acid is needed to be controlled at a concentration in a reaction fluid of not more than a specific value by adding the keto acid in portions or continuously.

Patent Document 1: JP-A Hei10-23896
Patent Document 2: WO 95/093081
Non-Patent Document 1: Ramesh N. Patel, "Enzymatic synthesis of chiral intermediates for Omapatrilat, an antihypertensive drug", Biomolecular Engineering, 2001, No. 17, p. 167.

DISCLOSURE OF THE INVENTION

Problems to be Solved by the Invention

The present inventors found out that use of a keto acid with low purity as a substrate in a reductive amination may lead to low productivity of the reaction.

An object of the present invention is to provide a method for efficiently producing an L-amino acid independent of the purity of the substrate in the reductive amination.

Means for Solving the Problems

In view of the above-mentioned problems, the present inventors conducted intensive studies to find out that in a reaction in which a keto acid corresponding to a target amino acid is reacted with an amino acid dehydrogenase and an enzyme having coenzyme regenerating ability to convert to the target L-amino acid (reductive amination), addition of a coenzyme to a reaction fluid in two or more portions makes it possible to avoid low productivity due to a low yield of the L-amino acid and the like, caused by use of the keto acid with low purity as the substrate. Accordingly, the present inventors have completed the present invention.

Namely, the present invention is characterized as follows.

One aspect of the present invention is a method for producing an L-amino acid, which comprises reacting a keto acid represented by the following formula (1):

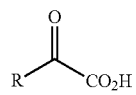

(1)

(wherein R is an unsubstituted or substituted C1-C20 alkyl group, an unsubstituted or substituted C7-C20 alalkyl group, or an unsubstituted or substituted C6-C20 aryl group)
with an amino acid dehydrogenase and an enzyme having coenzyme regenerating ability to convert to an L-amino acid represented by the following formula (2):

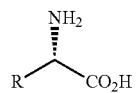

(2)

wherein R is the same as described above,
wherein a coenzyme is added in two or more portions in the reaction.

Another aspect of the present invention is the above-mentioned method for producing an L-amino acid, wherein the purity of the keto acid is 95% or less.

Still another aspect of the present invention is the above-mentioned method for producing an L-amino acid, wherein an amount of the coenzyme added at the beginning of the reaction is not more than ¾ of the total amount of the coenzyme added through the reaction.

Still another aspect of the present invention is the above-mentioned method for producing an L-amino acid, wherein the amount of the coenzyme per portion is not more than ½ of the total amount of the coenzyme added through the reaction.

Still another aspect of the present invention is the above-mentioned method for producing an L-amino acid, wherein the coenzyme is continuously added.

EFFECT OF THE INVENTION

The present invention is designed as described above, and can efficiently produce an L-amino acid independent of the purity of the substrate keto acid.

BEST MODE FOR CARRYING OUT THE INVENTION

Hereafter, the present invention is described in detail based on an embodiment. The scope of the present invention is not limited to the embodiment and the examples.

1. Type of Keto Acid Used as Substrate in Reductive amination

Examples of the substrate used in the reductive amination of the present invention include keto acids represented by the following formula (1):

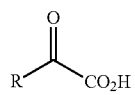
(1)

wherein R is an unsubstituted or substituted C1-C20 alkyl group, an unsubstituted or substituted C7-C20 alalkyl group, or an unsubstituted or substituted C6-C20 aryl group.

The unsubstituted or substituted C1-C20 alkyl group as the R is not particularly limited, and examples thereof include methyl group, isopropyl group, isobutyl group, 1-methylpropyl group, carbamoyl methyl group, 2-carbamoyl ethyl group, hydroxymethyl group, 1-hydroxyethyl group, mercaptomethyl group, 2-methylthioethyl group, (1-mercapto-1-methyl)ethyl group, 4-amino butyl group, 3-guanidino propyl group, 4(5)-imidazole methyl group, ethyl group, n-propyl group, n-butyl group, t-butyl group, 2,2-dimethyl propyl group, chloromethyl group, methoxymethyl group, 2-hydroxyethyl group, 3-aminopropyl group, 2-cyanoethyl group, 3-cyanopropyl group, 4-(benzoylamino) butyl group, 2-methoxy carbonylethyl group, and the like.

The unsubstituted or substituted C7-C20 alalkyl group is not particularly limited, and examples thereof include benzyl group, indolylmethyl group, 4-hydroxybenzyl group, 2-fluorobenzyl group, 3-fluorobenzyl group, 4-fluorobenzyl group, 3,4-methylenedioxybenzyl group, and the like.

Examples of the unsubstituted or substituted C6-C20 aryl group include phenyl group, 4-hydroxyphenyl group, and the like.

Examples of the substituent include amino group, hydroxyl group, nitro group, cyano group, carboxyl group, alkyl group, aralkyl group, aryl group, alkanoyl group, alkenyl group, alkynyl group, alkoxyl group, halogen atoms, and the like.

The keto acid may contain impurities such as by-products formed upon production of the keto acid and keto acid decomposed products. Examples of the impurities include mineral acids such as hydrochloric acid and sulfuric acid; organic acids such as formate and acetic acid; metals such as sodium, potassium, magnesium, calcium, iron, lithium, manganese, zinc, and copper, and salts thereof; organic solvents such as methanol, ethanol, ethyl acetate, acetone, toluene, chloroform, and n-hexane; and the like.

Examples of the keto acid decomposed products include carboxylic compounds represented by the following formula (3)

wherein R is the same as described above. The carboxylic compounds are produced by decarboxylation of the keto acid.

Use of a keto acid with low purity due to such impurities as a substrate in a later-described reductive amination may lead to low productivity of the reaction (see Reference Example 1 and Comparative Example 1). The productivity of the reaction is determined to be low in cases such as a low yield of a target L-amino acid, and a long reaction time.

The purity of the keto acid described here is represented by a ratio of the weight of the keto acid contained in a keto acid product to the weight of the dried keto acid product.

2. Enzyme Used in Reductive Amination

Next, an enzyme used in the reductive amination is described. Amino acid dehydrogenases have activity to reductively aminate a keto acid or a cyclic imine, and examples thereof include phenylalanine dehydrogenase, leucine dehydrogenase, and pyrroline-2-carboxylate reductase, and the like.

These amino acid dehydrogenases require a reduced coenzyme such as NADH in the reaction, and the coenzyme NADH is converted to the oxidized form in a process of the reaction. The amount of the coenzyme to be used can be significantly reduced by allowing the reaction of an enzyme having ability to convert the oxidized coenzyme to the reduced form (hereinafter, referred to coenzyme regenerating ability) and a substrate compound of the enzyme having coenzyme regenerating ability to proceed under the presence of the amino acid dehydrogenase.

Examples of the enzyme having coenzyme regenerating ability include hydrogenases, formate dehydrogenase, alcohol dehydrogenases, aldehyde dehydrogenases, glucose-6-phosphate dehydrogenase, glucose dehydrogenases, and the like. Formate dehydrogenase is suitably used.

The amino acid dehydrogenase and enzyme having coenzyme regenerating ability used in the present invention may be animal-derived, plant-derived, or microorganism-derived. However, microorganism-derived enzymes are desirable for industrial use.

Examples of microorganisms capable of producing the amino acid dehydrogenase include known microorganisms capable of producing the enzyme belonging to the genera: *Brevibacterium, Rhodococcus, Sporosarcina, Thermoactinomyces, Microbacterium, Halomonas, Clostridium, Bacillus, Neurospora, Escherichia,* and *Aerobacter,* and other microorganisms.

Enzymes derived from microorganisms belonging to the genus *Bacillus* are desirable. An enzyme derived from *Bacillus badius* IAM11059, or an enzyme derived from *Bacillus sphaericus* NBRC3341 is more desirably used.

The microorganism *Bacillus badius* IAM11059 produces phenylalanine dehydrogenase, and is described in EP 256514 and Biosci. Biotechnol. Biochem., 1995, Volume 59, No. 10, p. 1994.

The microorganism *Bacillus sphaericus* NBRC 3341 produces leucine dehydrogenase. Leucine dehydrogenase from *Bacillus sphaericus* NBRC 3341 has the same number of amino acid residues and exactly the same amino acid sequence as those of the known enzyme leucine dehydrogenase from *Bacillus subtilis*, but has 14 different bases among 1095 bases in the gene sequence.

The gene sequence of *Bacillus subtilis* is available in Nature, 1997 volume 390, p. 249 and at NCBI database (accession number CAB14339). The following document discloses that microorganisms belonging to the genera *Neurospora*, *Escherichia*, or *Aerobacter* produce pyrroline-2-carboxylate reductase (Methods Enzymol., 1962, volume 5, p. 882).

Examples of the microorganisms capable of producing formate dehydrogenase include known microorganisms capable of producing the enzyme belonging to the genera: *Candida*, *Kloeckera*, *Pichia*, *Lipomyces*, *Pseudomonas*, *Moraxella*, *Hyphomicrobium*, *Paracoccus*, *Thiobacillus*, and *Ancylobacter*, and the like.

Thiobacillus- or Ancylobacter-derived enzymes are desirable. An enzyme derived from *Thiobacillus* sp. KNK65MA (FERM BP-7671) and an enzyme derived from *Ancylobacter aquaticus* KNK607M (FERM BP-7335) are more desirable.

In order to obtain a highly active microorganism capable of efficient production of the respective enzymes, preparation of a transformed microorganism is advantageous as known to those skilled in art. The transformed microorganism is prepared, for example, as follows: cloning a leucine dehydrogenase gene obtained from a strain having leucine dehydrogenase activity; generating a recombinant plasmid using a suitable vector; and transforming a host microorganism such as, but not particularly limited to, *Escherichia coli* using the recombinant plasmid to prepare a transformant.

As the vector, a plasmid or phage derived from a microorganism that can automatically replicate in the host, or a derivative thereof can be used. Especially, for example, *Escherichia coli* for transformation, whose bacteriological characteristics are known to those skilled in art, is desirably used as the host organism, and a vector that can automatically replicate in the organism is desirably used as the vector.

Examples of such vectors include vectors easily available to those skilled in the art or commercially available vectors, such as pUC18 (Takara Bio, Inc.), pUC19 (Takara Bio, Inc.), pBR322 (Takara Bio, Inc.), pACYC184 (NIPPON GENE Co., Ltd.), pSTV28 (Takara Bio, Inc.), pSTV29 (Takara Bio, Inc.), pSC101 (Funakoshi Corp.), pT7Blue (Takara Bio, Inc.), and pUCNT that can be prepared by those skilled in the art based on the description of WO 94/03613, and derivatives thereof.

The derivatives include vectors in which a promoter, a terminator, an enhancer, SD sequence, a replication initiation site (ori), or another regulatory gene is modified for the purposes to increase production of the enzymes and stabilize the plasmid, and vectors in which a drug resistance gene, or a restriction enzyme site in the cloning site is modified.

Examples of the transformants thus obtained include *Escherichia coli* HB101 (pFT001) (FERM BP-7672) containing the formate dehydrogenase gene derived from *Thiobacillus* sp. KNK65MA (FERM BP-7671), *Escherichia coli* HB101 (pFT002) (FERM BP-7673) containing the same (see, WO 03/031626), and the like.

The recombinant DNA techniques used in the present invention are known in the field, and described in, for example, Molecular Cloning 2nd Edition (Cold Spring Harbor Laboratory Press, 1989), and Current Protocols in Molecular Biology (Greene Publishing Associates and Wiley-Interscience).

Culturing of the transformant and the like enables large-scale production of the enzymes, and the enzymes can be used for production of L-amino acids. A microorganism may be cultured using a general culture medium. A general culture medium containing nutrients such as carbon sources, nitrogen sources, and inorganic salts can be used for the culturing. Addition of trace organic nutrients such as vitamins and amino acids in many cases produces a favorable result. Examples of the suitable carbon sources include carbohydrates such as glucose and sucrose, organic acids such as acetic acid, and alcohols, and the like. Examples of the nitrogen sources include ammonium salts, ammonia solution, ammonia gas, urea, yeast extract, peptone, corn steep liquors, and the like. Examples of the inorganic salts include phosphates, magnesium salts, potassium salts, sodium salts, calcium salts, iron salts, sulfates, chlorine, and the like.

The culture temperature may be in a range of from 25° C. to 40° C., and particularly desirably from 25° C. to 37° C. The culture pH may be in a range of from 4 to 8, and desirably from 5 to 7.5. Either a batch culturing method or a continuous culturing method may be used.

A treatment for inducing the enzymes such as addition of isopropyl-1-thio-β-D-galactoside (IPTG), lactose or the like may also be performed, if necessary.

3. Reductive Amination

Next, a method for producing an L-amino acid from a keto acid by a reductive amination is described. In the reductive amination, the keto acid, the above-mentioned amino acid dehydrogenase, the enzyme having coenzyme regenerating ability and a substrate compound of the enzyme are all present together, and allowed to react in an aqueous medium.

The amino acid dehydrogenase and the enzyme having coenzyme regenerating ability used in the present invention may be produced by culturing microorganisms each having activity of either enzyme, or preparing transformants into each of which either of the enzyme genes is introduced, and culturing the transformants. Alternatively, the amino acid dehydrogenase and the enzyme having coenzyme regenerating ability used in the present invention may be produced by preparing a transformant into which the plural enzyme genes are introduced, and culturing the transformant.

In the present invention, the produced amino acid dehydrogenase and the produced enzyme having coenzyme regenerating ability can be used per se, or may be contained in the microorganism(s) or in a microorganism processed product. Here, the microorganism processed product is defined as a product having the target enzyme activity such as crude extract, cultured cells, a lyophilized organism, an acetone-dried organism and disrupted cells thereof.

They may be used in the form of an immobilized enzyme obtained by immobilizing the enzymes or the cells themselves by a well-known method such as crosslinking, covalent binding, physical adsorption, or an entrapment method.

Addition of a coenzyme such as NAD to the above-mentioned reductive amination is expected to improve the efficiency of the reaction. The coenzyme such as NAD is added desirably at a concentration of from 0.000001 equivalents to 2 equivalents with respect to the substrate, more desirably from 0.00001 equivalents to 0.1 equivalents, further more desirably from 0.0001 equivalents to 0.01 equivalents. The upper limit of the amount of the coenzyme to be added is not particularly limited, but typically is 2 equivalents or less, desirably 0.1 equivalents or less, more desirably 0.01 equivalents or less for economical reasons.

In the case where a keto acid with low purity that leads to low productivity of the reaction as described in the preceding section 1 is used as the substrate, addition of the coenzyme such as NAD in two or more portions can improve the productivity of the reaction (addition in portions), compared to addition of all in one portion at the beginning of the reaction (addition in one portion) (see Example 1 and Comparative Example 1). The productivity is determined to be improved in cases such as an improved yield of a target L-amino acid and a short reaction time. Even in the case where such a keto acid with low purity is used as the substrate and the entire amount of the coenzyme is added in one portion at the beginning of the reaction, the productivity of the reaction can be improved by adding a large amount of the coenzyme. However, addition of the coenzyme in portions can reduce the total amount of the coenzyme to be added.

When the coenzyme is added in portions, the amount of the coenzyme added at the beginning of the reaction is desirably ¾ or less of the total amount of the coenzyme to be added through the reaction, more desirably ⅔ or less, further more desirably ½ or less, still further more desirably ⅓, ¼ or less of the total amount.

In addition, when the coenzyme is added in portions, the amount of the coenzyme added in each portion is desirably ⅔ or less of the total amount of the coenzyme to be added through the reaction, more desirably ½ or less, furthermore desirably ⅓ or less, still further more desirably ¼ or less of the total amount.

When added in portions, the coenzyme is added desirably in two or more portions, more desirably three or more portions, further more desirably four or more portions. Here, the coenzyme can also be continuously added during the reaction.

The addition of the coenzyme in portions is effective in improving productivity of the reaction when using a substrate with a purity of not more than 95%, more effective when using a substrate with a purity of not more than 90%, further more effective when a substrate with a purity of not more than 85%.

The keto acid serving as the substrate of the reductive amination is dissolved or suspended at a loading concentration of from 0.1% (w/v) to 90% (w/v), desirably from 1% (w/v) to 60% (w/v), and then the reaction is allowed to proceed with a temperature kept in a suitable range of from 10° C. to 80° C., desirably from 20° C. to 60° C., while the reaction fluid is allowed to stand or stirred for a certain period of time.

During the reaction, the pH is desirably adjusted in a range of from 4 to 12, more desirably in a range of from 6 to 11. The pH can be adjusted by adding an acid or a base. The substrate of the reaction may be added in one portion or in two or more portions, or may be continuously added. Either a batch method or a continuous method can be used for the above-mentioned reductive amination.

An immobilized enzyme, a membrane reactor or the like can be used in the reductive amination of the present invention. Examples of the aqueous medium include water, buffer solutions and aqueous media containing water or the buffer solution and a water soluble organic solvent such as ethanol. Other examples of the aqueous medium include media consisting of two phases of the above-mentioned aqueous medium and an organic solvent hardly soluble in water such as ethyl acetate, butyl acetate, toluene, chloroform, and n-hexane, and other suitable solvents. In addition, an antioxidant, a surfactant, a metal or the like may also be added, if necessary.

The L-amino acid produced through the reductive amination can be isolated, or separated and purified by a conventional separation method such as extraction, concentration, crystallization or column chromatography, or a combination thereof.

EXAMPLE

The following examples illustrate the present invention in detail. However, the present invention is not limited to these examples.

Comparative Example 1

Synthesis of L-tert-Leucine by Reductive amination (Addition of Coenzyme in One Portion)

A transformant having leucine dehydrogenase activity and formate dehydrogenase activity was prepared following the procedure described below in Reference Example 4. The transformant was inoculated into a sterilized medium A (triptone 1.6%, yeast extract 1.0%, sodium chloride 0.5%, and ampicillin 0.01% dissolved in deionized water (ampicillin was added after sterilization), pH prior to sterilization: 7.0), and then aerobically cultured with shaking for 48 hours at 33° C.

The obtained culture fluid was centrifuged to collect cells, and the cells were suspended in deionized water to obtain a cell concentrate.

To 96.2 mg of trimethyl pyruvic acid with a purity of 83.2% were added the cell concentrate and ammonium formate in an amount of 1.4 molar equivalents with respect to the trimethyl pyruvic acid. In addition, 5M ammonia solution was added to adjust the pH of the fluid to 8.0, and deionized water was added to prepare 2 ml of a reaction fluid. To the reaction fluid, NAD in an amount of 0.0009 molar equivalents with respect to the trimethylpyruvic acid was added, and the reaction was allowed to proceed for 21.5 hours at 30° C. while being stirred.

Remaining trimethylpyruvic acid and produced L-tert-leucine were analyzed using high performance liquid chromatography (HPLC) for the residual ratio, and the optical purity and the yield, respectively. The results reveal that the residual ratio of trimethylpyruvic acid was 18.8 mol %, while the yield and the optical purity of L-tert-leucine were 81.1 mol % and 99% e.e. or more, respectively.

The yield of L-tert-leucine was lower and the residual ratio of trimethylpyruvic acid was higher compared to the case where trimethylpyruvic acid with high purity was used (Reference Example 1).

(HPLC Analysis Condition of Trimethyl Pyruvic Acid)

Column: COSMOSIL 5C18-AR (4.6 mm×250 mm, produced by Nacalai Tesque, Inc.), Mobile phase: 10 mM potassium phosphate buffer solution (pH 2.0)/acetonitrile=95/5, Flow rate: 1 ml/minute, Column temperature: 40° C., Detection: 210 nm.

(HPLC Analysis Condition of L-tert-Leucine)

Column: SUMICHIRAL OA-5000 (4.6 mm×250 mm, produced by Sumika Chemical Analysis Service, Ltd.), Mobile phase: 2 mM copper sulfate solution/methanol=95/5, Flow rate: 1 ml/minute, Column temperature: 35° C., Detection: 254 nm.

Example 1

Synthesis of L-tert-Leucine by Reductive Amination (Addition of Coenzyme in Portions)

To 96.2 mg of trimethylpyruvic acid with a purity of 83.2% used in Comparative Example 1 were added the cell concentrate of the transformant having leucine dehydrogenase activity and formate dehydrogenase activity in the same amount as used in Comparative Example 1, and ammonium formate in an amount of 1.4 molar equivalents with respect to trimethylpyruvic acid. In addition, 5M ammonia solution was added to adjust the pH of the fluid to 8.0, and deionized water was added to prepare 2 ml of a reaction fluid. To the reaction fluid, NAD in an amount of 0.0003 molar equivalents with respect to trimethylpyruvic acid was added, and stirred at 30° C.

NAD in an amount of 0.0003 molar equivalents with respect to the substrate was added 3 and 6 hours after the beginning of the reaction, respectively, and the reaction was allowed to proceed for 21.5 hours.

Remaining trimethylpyruvic acid and produced L-tert-leucine were analyzed for the residual ratio, and the optical purity and the yield, respectively, by following the same procedure as in Comparative Example 1. The results reveal that the residual ratio of trimethylpyruvic acid was 0.4 mol %, the yield and the optical purity of L-tert-leucine were 104.3 mol % and 99% e.e. or more, respectively.

The yield of L-tert-leucine was higher and the residual ratio of trimethylpyruvic acid was lower compared to the case where the coenzyme was added in one portion (Comparative Example 1).

Reference Example 1

Synthesis of L-tert-Leucine by Reductive Amination

To 81.2 mg of trimethylpyruvic acid with a purity of 98.5% were added the cell concentrate of the transformant having leucine dehydrogenase activity and formate dehydrogenase activity in the same amount as used in Comparative Example 1, and ammonium formate in an amount of 1.4 molar equivalents with respect to trimethylpyruvic acid. In addition, 5M ammonia solution was added to adjust the pH of the fluid to 8.0, and deionized water was added to prepare 2 ml of a reaction fluid.

To the reaction fluid was added NAD in an amount of 0.0009 molar equivalents with respect to the substrate, and the reaction was allowed to proceed for 22 hours at 30° C. while being stirred.

Analysis was performed by following the same procedure as in Comparative Example 1, and the results reveal that trimethylpyruvic acid had disappeared and L-tert-leucine was produced at a conversion ratio of 96.4 mol % with an optical purity of 99% e.e. or more.

Reference Example 2

Preparation of Transformant Having Formate Dehydrogenase Activity

PCR was carried out using a genome of *Thiobacillus* sp. KNK65MA (FERMBP-7671) as a template, and DNA primers (Primer-1: SEQ ID NO: 1 in the sequence listing, and Primer-2: SEQ ID NO: 2 in the sequence listing).

PCR was carried out as follows: To 100 ng of the template DNA were added 1.25 U (0.25 µl) of Pyrobest DNA polymerase (produced by Takara Bio, Inc.), 5 µl of 10× Pyrobest Buffer II (produced by Takara Bio, Inc.), 4 µl of a dNTP solution (2.5 mM each dNTP), 2 µl each of 20 µM primer solutions. Sterile water was also added to obtain 50 µl of a reaction fluid in total. Heat denaturation (96° C., 30 seconds), annealing (50° C., 30 seconds), and an extension reaction (72° C., 90 seconds) were repeated for 25 cycles, and then the reaction fluid was cooled to 4° C.

The DNA fragment obtained by PCR was cleaved by restriction enzymes NdeI and EcoRI, and ligated using T4 DNA ligase to a vector plasmid pUCNT (those skilled in the art can produce based on Description of WO 94/03613) cleaved by the enzymes. Thus, a plasmid designed to express a large amount of formate dehydrogenase was prepared.

The obtained plasmid was transformed into competent cells of *Escherichia coli* HB101. Thus, a transformant having formate dehydrogenase activity was prepared.

The obtained transformant was inoculated into 6 ml of a sterilized medium A in a test tube, and aerobically cultured with shaking for 24 hours at 37° C.

The obtained culture fluid was centrifuged to collect cells, and the plasmid was extracted using a QIAprep Spin Miniprep Kit (produced by QIAGEN). Thus, plasmids designed to express a large amount of formate dehydrogenase were retrieved.

Reference Example 3

Preparation of Transformant Having Leucine Dehydrogenase Activity

PCR was carried out using a genome of *Bacillus sphaericus* NBRC 3341 as a template, and DNA primers (Primer-3: SEQ ID NO: 3 in the sequence listing, and Primer-4: SEQ ID NO: 4 in the sequence listing) under the same conditions as used in Reference Example 2.

The DNA fragment obtained by PCR was cleaved by restriction enzymes EcoRI and SacI, and ligated using T4 DNA ligase to a vector plasmid pUCT (a plasmid vector obtained by destroying the NdeI recognition sequence of pUCNT (those skilled in the art can produce based on Description of WO 94/03613) by one base substitution) cleaved by the enzymes. Thus, a plasmid designed to express a large amount of leucine dehydrogenase was prepared.

The obtained plasmid was transformed into competent cells of *Escherichia coli* HB101. Thus, a transformant having leucine dehydrogenase activity was prepared.

The obtained transformant was inoculated into 6 ml of a sterilized medium A in a test tube, and aerobically cultured with shaking for 24 hours at 37° C.

The obtained culture fluid was centrifuged to collect cells, and the plasmid was extracted using a QIAprep Spin Miniprep Kit (produced by QIAGEN). Thus, plasmids designed to express a large amount of leucine dehydrogenase were retrieved.

Reference Example 4

Preparation of Transformant Having Leucine Dehydrogenase Activity and Formate Dehydrogenase Activity The plasmid designed to express a large amount of leucine dehydrogenase prepared in Reference Example 3 was cleaved by restriction enzymes EcoRI and PstI, and a DNA fragment containing the leucine dehydrogenase gene was retrieved using TaKaRaRECOCHIP (produced by Takara Bio, Inc.).

The plasmid designed to express a large amount of formate dehydrogenase prepared in Reference Example 2 was also cleaved at the EcoRI and PstI sites downstream of the formate dehydrogenase gene to obtain a DNA fragment. This DNA fragment was ligated to the above-mentioned DNA fragment containing the leucine dehydrogenase gene using T4 DNA ligase. Thus, the plasmid designed to express large amounts of leucine dehydrogenase and formate dehydrogenase was prepared.

The obtained plasmid was transformed into competent cells of *Escherichia coli* HB101. Thus, a transformant having leucine dehydrogenase activity and formate dehydrogenase activity was prepared.

The invention claimed is:

1. A method for producing an L-amino acid, by beginning a reaction which comprises contacting a keto acid contained in a dried keto acid containing product; wherein the keto acid is represented by the following formula (1):

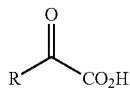
(1)

wherein R is an unsubstituted or substituted C1-C20 alkyl group, an unsubstituted or substituted C7-C20 aralkyl group, or an unsubstituted or substituted C6-C20 aryl group;

with a reaction milieu comprising an amino acid dehydrogenase and an enzyme having coenzyme regenerating ability to convert to an L-amino acid represented by the following formula (2):

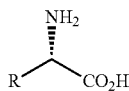
(2)

wherein R is the same as described above, wherein a coenzyme is added continuously, or in two or more portions to the reaction, and wherein the purity of the keto acid is 90% or less, wherein the purity of the keto acid is the ratio of the weight of the keto acid contained in the keto acid product to the weight of the dried keto acid product, wherein the amino acid dehydrogenase is obtainable from microorganisms selected from the group consisting of the genera: *Brevibacterium, Rhodococcus, Sporosarcina, Thermoactinomyces, Microbacterium, Halomonas, Clostridium, Bacillus, Neurospora, Escherichia*, and *Aerobacter*, wherein the unsubstituted or substituted C1-C20 alkyl group as the R group is selected from the group consisting of methyl, isopropyl, isobutyl, 1-methylpropyl, carbamoyl methyl, 2-carbamoyl ethyl, hydroxymethyl, 1-hydroxyethyl, mercaptomethyl, 2-methylthioethyl, (1-mercapto-1-methyl)ethyl, 4-amino butyl, 3-guanidino propyl, 4(5)-imidazole methyl, ethyl, n-propyl, n-butyl, t-butyl, 2,2-dimethyl propyl, chloromethyl, methoxymethyl, 2-hydroxyethyl, 3-aminopropyl, 2-cyanoethyl, 3-cyanopropyl, 4-(benzoylamino) butyl, and 2-methoxy carbonylethyl, and wherein the unsubstituted or substituted C7-C20 aralkyl group as the R group is selected from the group consisting of benzyl, indolylmethyl, 4-hydroxybenzyl, 2-fluorobenzyl, 3-fluorobenzyl, 4-fluorobenzyl, and 3,4-methylenedioxybenzyl.

2. The method according to claim 1,
wherein an amount of the coenzyme added at the beginning of the reaction is not more than ¾ of the total amount of the coenzyme added through the reaction.

3. The method according to claim 2,
wherein the amount of the coenzyme added at the beginning of the reaction is not more than ½ of the total amount of the coenzyme added through the reaction.

4. The method according to claim 2,
wherein the coenzyme is continuously added.

5. The method according to claim 2,
wherein the coenzyme is NAD.

6. The method according to claim 2,
wherein the L-amino acid is L-tert-leucine or L-4-methylleucine.

7. The method according to claim 2,
wherein the amino acid dehydrogenase is leucine dehydrogenase or phenylalanine dehydrogenase.

8. The method according to claim 2,
wherein the enzyme having a coenzyme regenerating ability is formate dehydrogenase or glucose dehydrogenase.

9. The method according to claim 1,
wherein the amount of the coenzyme added per portion is not more than ½ of the total amount of the coenzyme added through the reaction.

10. The method according to claim 9,
wherein the coenzyme is continuously added.

11. The method according to claim 9,
wherein the coenzyme is NAD.

12. The method according to claim 9,
wherein the L-amino acid is L-tert-leucine or L-4-methylleucine.

13. The method according to claim 9,
wherein the amino acid dehydrogenase is leucine dehydrogenase or phenylalanine dehydrogenase.

14. The method according to claim 1,
wherein the coenzyme is NAD.

15. The method according to claim 6,
wherein the L-amino acid is L-tert-leucine or L-4-methylleucine.

16. The method according to claim 14,
wherein the amino acid dehydrogenase is leucine dehydrogenase or phenylalanine dehydrogenase.

17. The method according to claim 1,
wherein the L-amino acid is L-tert-leucine or L-4-methylleucine.

18. The method according to claim 17,
wherein the amino acid dehydrogenase is leucine dehydrogenase or phenylalanine dehydrogenase.

19. The method according to claim 1,
wherein the amino acid dehydrogenase is leucine dehydrogenase or phenylalanine dehydrogenase.

20. The method according to claim 1,
wherein the enzyme having a coenzyme regenerating ability is formate dehydrogenase or glucose dehydrogenase.

* * * * *